United States Patent [19]

Inoue et al.

[11] Patent Number: 5,327,474
[45] Date of Patent: Jul. 5, 1994

[54] X-RAY RADIOGRAPHIC APPARATUS FOR MEDICAL USE

[75] Inventors: Yoshihiro Inoue, Higashi; Katsunori Sukeyasu, Nagaokakyo; Yoshitaka Okumura, Kyoto, all of Japan

[73] Assignee: Shimadzu Corporation, Kyoto, Japan

[21] Appl. No.: 21,855

[22] Filed: Feb. 24, 1993

[30] Foreign Application Priority Data

Feb. 28, 1992 [JP] Japan ..................... 4-079146

[51] Int. Cl.$^5$ ............................................ H05G 1/60
[52] U.S. Cl. ..................... 378/20; 378/116; 378/193; 378/196
[58] Field of Search ............... 378/4, 10, 19, 20, 193, 378/195, 196, 197, 198, 114–116

[56] References Cited

U.S. PATENT DOCUMENTS

| | | | |
|---|---|---|---|
| 4,501,011 | 2/1985 | Hauck et al. | 378/197 |
| 4,672,454 | 6/1987 | Cannella et al. | 358/213.11 |
| 5,199,060 | 3/1993 | Kato | 378/195 |

FOREIGN PATENT DOCUMENTS

| | | | |
|---|---|---|---|
| 0373596 | 6/1990 | European Pat. Off. | |
| 0016197 | 2/1979 | Japan | 378/20 |
| WO89/04996 | 6/1989 | World Int. Prop. O. | |

OTHER PUBLICATIONS

Patent abstracts of Japan, vol. 13, No. 241, Jun. 6, 1989.

*Primary Examiner*—David P. Porta
*Attorney, Agent, or Firm*—Nikaido, Marmelstein, Murray & Oram

[57] ABSTRACT

An X-ray radiographic apparatus for medical use in photographing tomographic images and X-ray penetration images of an examinee. This apparatus has a bed horizontally movably supporting a top board for carrying the examinee, a gantry for X-ray tomography including a first X-ray source revolvable around the examinee and a first X-ray detector for detecting transmitted X-rays, a second X-ray source mounted on a moving mechanism movable on a three-dimensional coordinate system in an examination room accommodating the bed and the gantry, a high voltage unit for supplying an X-ray generating high current to the first X-ray source and the second X-ray source, a switch for selecting a destination of output of the high voltage unit, and a second X-ray detector for detecting transmitted X-rays from the second X-ray source.

10 Claims, 8 Drawing Sheets

X-RAY RADIOGRAPHIC APPARATUS FOR MEDICAL USE

BACKGROUND OF THE INVENTION (1) Field of the Invention

This invention relates to X-ray radiographic apparatus used in the medical field.

(2) Description of the Related Art

The X-ray radiographic apparatus used in the medical field may be classified, by the difference in images, broadly into an X-ray CT apparatus for photographing slice images of the body, and an ordinary X-ray radiographic apparatus, or what is known as a roentogenographic apparatus, for recording X-ray penetration images (planar images) of the body on X-ray film.

The X-ray CT apparatus causes an X-ray source to revolve around an examinee, and detects X-rays transmitted through the examinee. The detected X-rays are converted to a digital signal for image reconfiguration. The results are subjected to appropriate image processing such as enlargement or reduction to be shown on a monitor display. The examinee is transported on a horizontally movable bed to the apparatus.

The ordinary X-ray radiographic apparatus photographs an examinee lying on a bed, by means of an X-ray tube and X-ray film arranged vertically across the examinee. A different type of X-ray radiographic apparatus has, in place of the X-ray film, an image intensifier for converting X-rays to an optical image, and an X-ray television camera for picking up the optical image outputted from the image intensifier and converting the image to an electrical signal (video signal). The video signal is digitalized, and the result is subjected to appropriate image processing such as enlargement or reduction to be shown on a monitor display. A further type of X-ray radiographic apparatus has both the function to take photographs on film and the function to present pictures on a monitor display. These apparatus are collectively called hereinafter the ordinary X-ray radiographic apparatus.

While there is a physical difference between the images obtained from the X-ray CT apparatus and the ordinary X-ray radiographic apparatus, not a few components can be shared by the two types of apparatus which use the same principle of obtaining information about the body interior through X-ray exposure. Such components include the bed for supporting the examinee, a high voltage unit for supplying a high current to the X-ray tube to generate X-rays, an image processing unit for enlarging and reducing images shown on the monitor display, a console, and so on. The two types of apparatus are used for approximately the same purpose. Sometimes one patient is diagnosed by successively using the X-ray CT apparatus and ordinary X-ray radiographic apparatus.

However, the two apparatus are manufactured and sold separately as completely independent apparatus. In a medical organization having both apparatus, a large space must be secured to accommodate them at the same time or, as an alternative, a separate examination room must be secured to accommodate each apparatus. In the latter case, the patients diagnosed with the two apparatus must move from one examination room to the other. This imposes a considerable burden particularly on patients suffering from advanced diseases.

SUMMARY OF THE INVENTION

Having regard to the state of the art noted above, the object of this invention is to provide an X-ray radiographic apparatus which realizes accommodation of the above two apparatus (X-ray CT apparatus and ordinary X-ray radiographic apparatus) in an installation space suited substantially to a single apparatus.

The above object is fulfilled, according to this invention, by an X-ray radiographic apparatus for medical use in photographing tomographic images and X-ray penetration images of an examinee, the apparatus comprising a bed horizontally movably supporting a top board for carrying the examinee; a gantry for X-ray tomography including a first X-ray source revolvable around the examinee, and a first X-ray detector for detecting transmitted X-rays; a second X-ray source attached to a moving mechanism movable on a three-dimensional coordinate system in an examination room accommodating the bed and the gantry; a high voltage unit for supplying an X-ray generating high current to the first X-ray source and the second X-ray source; a switch for selecting a destination of output of the high voltage unit; and a second X-ray detector for detecting transmitted X-rays from the second X-ray source.

In the X-ray radiographic apparatus for medical use according to the present invention, the two X-ray sources share the high voltage unit for supplying a X-ray generating high current, as well as the bed for supporting the examinee. Since the second X-ray source is movable on a three-dimensional coordinate system in the examination room, the second X-ray detector may be installed in any desired position. With the second X-ray detector installed in an appropriate position, an installation space just about large enough for a single X-ray CT apparatus enables tomography using the first X-ray source and first X-ray detector, and X-ray radiography using the second X-ray source and second X-ray detector.

Consequently, two apparatus for the two types of photo taking need not be installed in separate examination rooms. The patient to be diagnosed by the two types of photo taking has a reduced burden without the necessity to move from one examination room to the other. The apparatus according to the present invention can, in all probability, be installed in a medical organization lacking in space for separately accommodating the two types of apparatus (since a space for one apparatus is sufficient), thereby to enhance diagnostic facilities.

The second X-ray detector may comprise a cassette containing X-ray film, an image intensifier for converting transmitted X-rays to an optical image, or a digital sensor having semiconductor elements arranged multi-dimensionally to detect transmitted X-rays.

The cassette or digital sensor may be vertically movably mountable in a wall of the gantry, in the bed, or on a Bucky's stand installed in an appropriate position in the examination room.

Where the second X-ray detector comprises a cassette or a digital sensor, the moving mechanism of the second X-ray source preferably includes a ceiling frame secured to a ceiling of the examination room, a movable frame movable within the ceiling frame, a support block movable within the movable frame in a direction perpendicular to a direction of movement of the movable frame, and a vertically extendible and contractible ceiling suspender having an upper end thereof secured to the support block. The second X-ray source is pivotably attached to a lower end of the ceiling suspender.

Where the second X-ray detector comprises a relatively heavy image intensifier, the moving mechanism of the second X-ray source preferably includes, besides the ceiling frame, movable frame and support block noted above, a C-shaped arm pivotably attached to the support block. The second X-ray source is attached to one end of the C-shaped arm, while the image intensifier is attached to the other end of the C-shaped arm.

BRIEF DESCRIPTION OF THE DRAWINGS

For the purpose of illustrating the invention, there is shown in the drawings a form which is presently preferred, it being understood, however, that the invention is not limited to the precise arrangements and instrumentalities shown.

DETAILED DESCRIPTION OF THE PREFERRED EMBODIMENTS

A preferred embodiment of this invention will be described in detail hereinafter with reference to the drawings.

Figure 1:
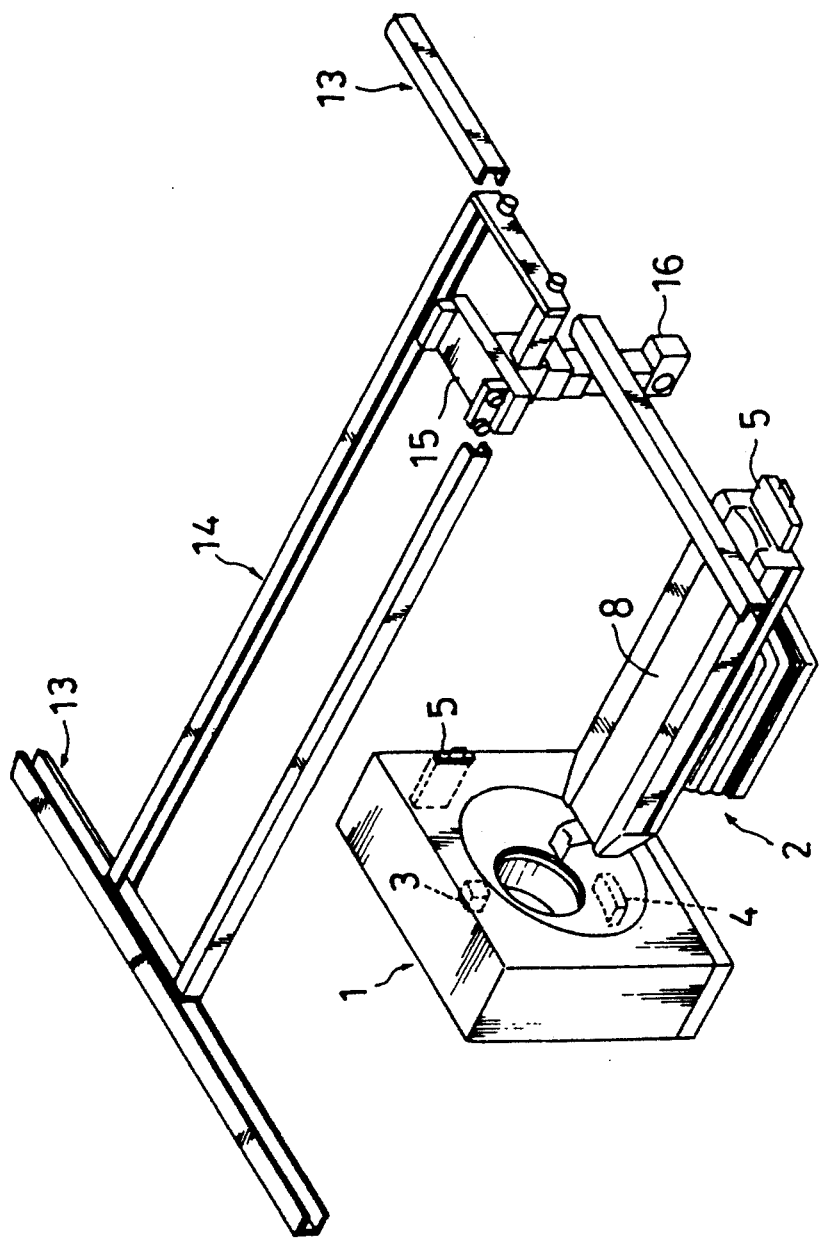
FIG. 1 is a perspective view showing an outward appearance of an X-ray radiographic apparatus embodying this invention.

FIG. 1 is a perspective view showing an outward appearance of an entire X-ray radiographic apparatus in this embodiment.

A gantry 1 of an X-ray CT apparatus and a bed 2 are installed on the floor of an examination room. The gantry 1 has an X-ray tube 3 (first X-ray source) and an X-ray detector (first X-ray detector) revolvable therein in an opposed relationship with each other. Further, a cassette 5 (second X-ray detector) containing X-ray film is vertically movable mounted in a front wall of the gantry 1.

The bed 2 is vertically movable relative to the floor, and has a top board 8 mounted thereon to be horizontally movable toward an examinee receiving opening 7 of the gantry 1. A hollow space is formed in a rear position of the bed 2 to receive the cassette 5. The cassette 5 is mounted therein as illustrated.

Figure 2:
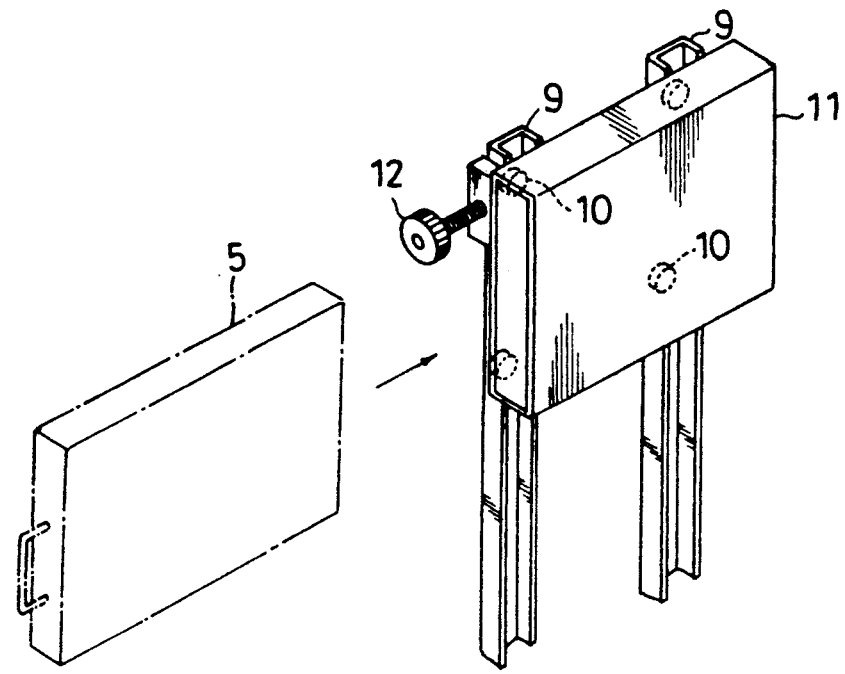
FIG. 2 is a perspective view showing a cassette slide mechanism.

The gantry 1 has a mechanism as shown in FIG. 2, for example, which is mounted on an lateral position inside the gantry 1 for vertically movably supporting the cassette 5.

This mechanism includes a pair of guide rails 9 having a U-shaped section, a case 11 for receiving the cassette 5 and having rollers 10 which roll along grooves of the guide rails 9, and a positioning screw 12 attached to the case 11.

The guide rails 9 are erected with the grooves thereof facing outwardly of the gantry 1. Thus, the cassette 5 is exposed to X-rays emitted from outside the gantry 1. An X-ray shielding lead sheet or the like is applied to a side surface of the case 11 opposed to the guide rails 9 (the side surface facing inwardly of the gantry 1), to avoid unnecessary exposure to the X-ray emitted from the X-ray tube 3 revolving inside the gantry 1.

Reverting to FIG. 1, a ceiling frame 13 is secured to a ceiling of the examination room. A movable frame 14 is attached to the ceiling frame 13 to be movable therein, and a support block 15 is attached to the movable frame 14 to be movable in the support block 15. The support block 15 supports an X-ray tube 16 (second X-ray source) suspended therefrom.

Figure 3:
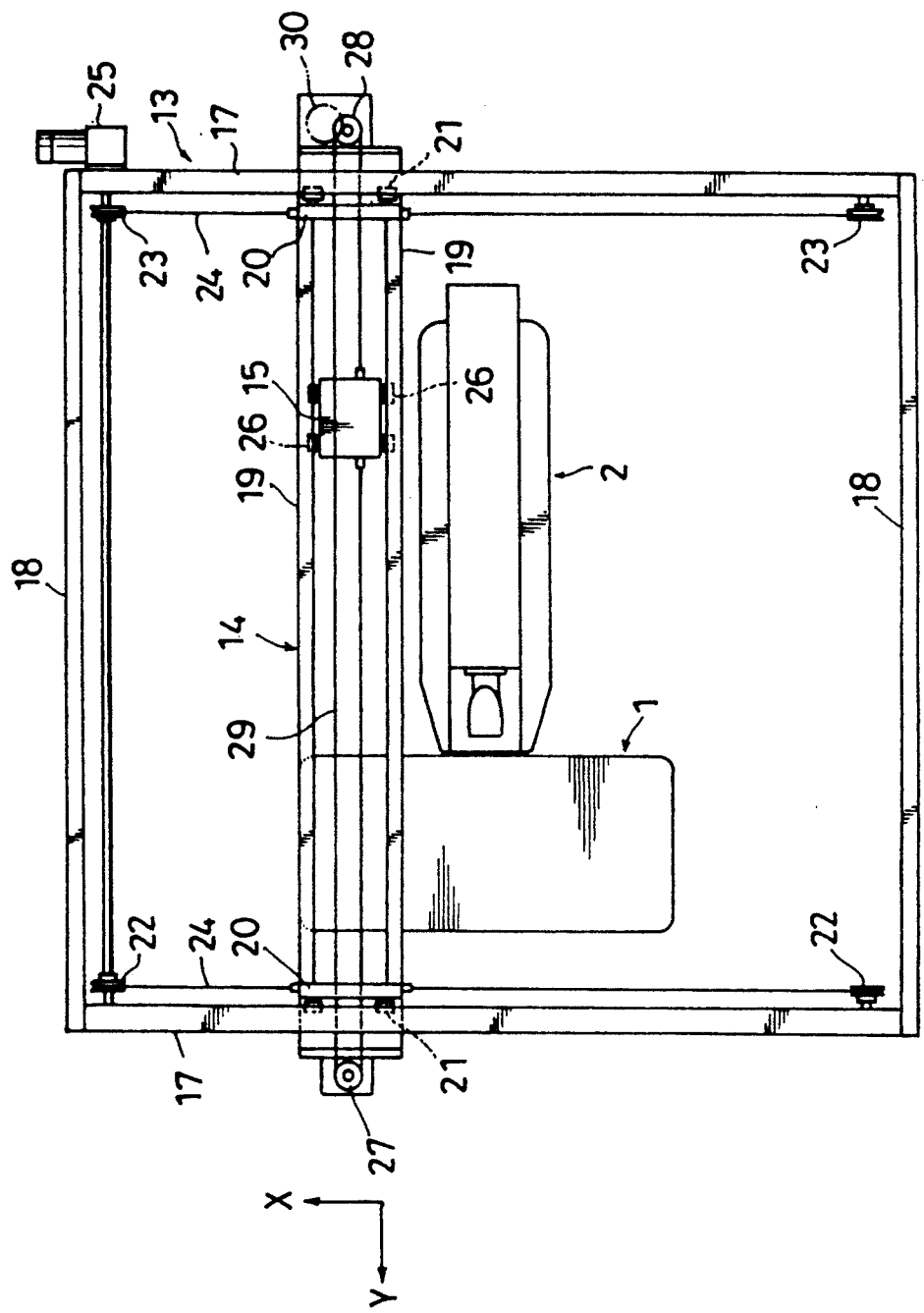
FIG. 3 is a plan view of the X-ray radiographic apparatus.

As shown in FIG. 3, the ceiling frame 13 includes two parallel guide rails 17 extending sideways (in the direction of X in FIG. 3) and interconnected through stays 18. Both of the guide rails 17 have a U-shaped section.

The movable frame 14 includes a pair of guide rails 19 extending fore and aft (in the direction of Y in FIG. 3) and interconnected through stays 20. Each stay 20 is opposed to the groove of one of the guide rails 17 forming part of the ceiling frame 13. A plurality of rollers 21 are rotatably attached to the opposed surface of the stay 20 for rolling along the groove.

The right and left stays 20 are connected, respectively, to wires 24 wound around two pairs of right and left pulleys 22 and 23 provided in fore and aft positions of the ceiling frame 13. The wires 24 are driven in fore and aft directions by a motor 25 to move the movable frame 14 in the fore and aft directions relative to the ceiling frame 13.

The support block 15 is movably supported in the movable frame 14 through a plurality of rollers 26 which roll along the grooves of the pair of guide rails 19 of the movable frame 14. The support block 15 is connected to a wire 29 wound around pulleys 27 and 28 disposed a left and right ends of the movable frame 14. The wire 29 is driven right and left by a motor 30 to move the support block 15 right and left relative to the movable frame 14.

Figure 4:
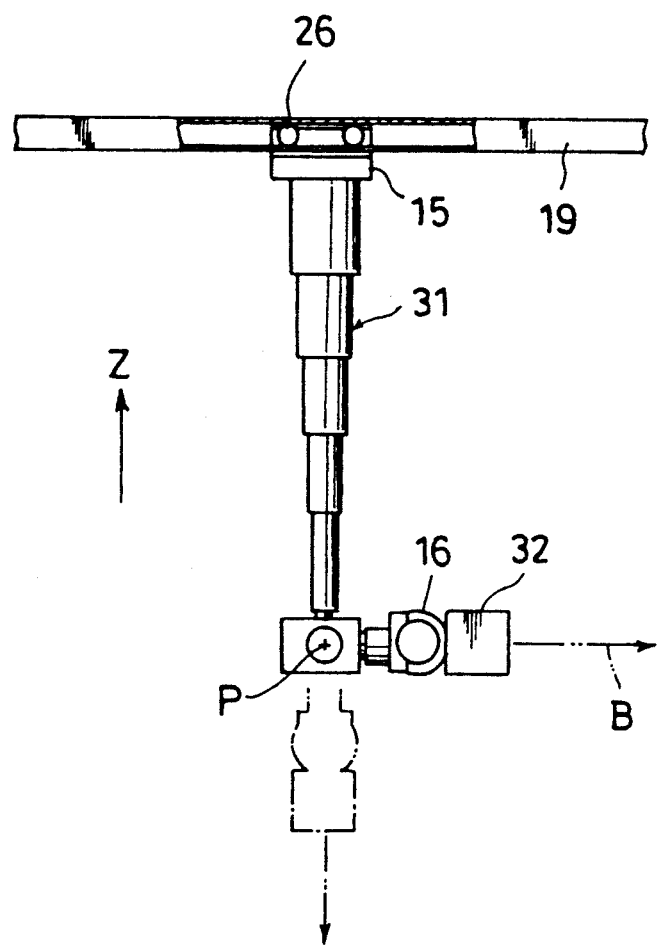
FIG. 4 is a front view showing a mounting mechanism of an X-ray tube (second X-ray source)

As shown in FIG. 4, the X-ray tube 16 is supported, to be pivotable through 90 degrees about an axis P, at a lower position of a ceiling suspender 31 vertically extendible and contractible (in the direction of Z in the drawing). An X-ray collimator 32 is attached to an X-ray emitting side of the X-ray tube 16 for adjusting an emission field of an X-ray beam B. Thus, the X-ray tube 16 is movable in each direction of a three-dimensional coordinate system X-Y-Z with reference to the examination room, to emit X-rays toward the cassette 5 mounted in the gantry 1 or in the bed 2.

Figure 5:
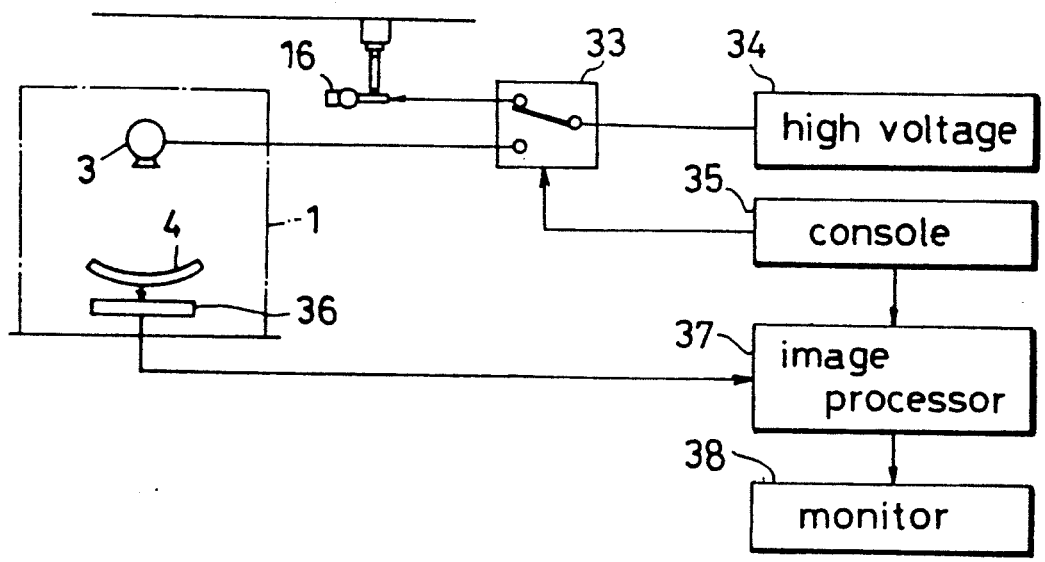
FIG. 5 is a block diagram schematically showing a system configuration of the X-ray radiographic apparatus.

FIG. 5 schematically shows a system configuration of the above X-ray radiographic apparatus.

The X-ray tube 3 provided in the gantry 1 of the CT apparatus and the X-ray tube 16 movable on the three-dimensional coordinate system in the examination room are connected through a switching circuit 33 to a high voltage unit 34. The switching circuit 33 is operable in response to control signals from a console 35, to select a destination of output of the high voltage unit 34.

The X-ray detector 4 opposed to the X-ray tube 3 in the gantry 1 for detecting transmitted X-rays is connected to a data collector 36 for collecting detection signals therefrom and converting them to digital signals. The data collector 36 is connected to an image processor 37.

The image processor 37 reconfigures a slice image from the digital signals transmitted from the data collector 36, enlarge or reduce the image in response to instructions from the console 35, and shows an image output on a monitor display 38.

Photographing modes of the above X-ray radiographic apparatus will be described next.

Figure 6:
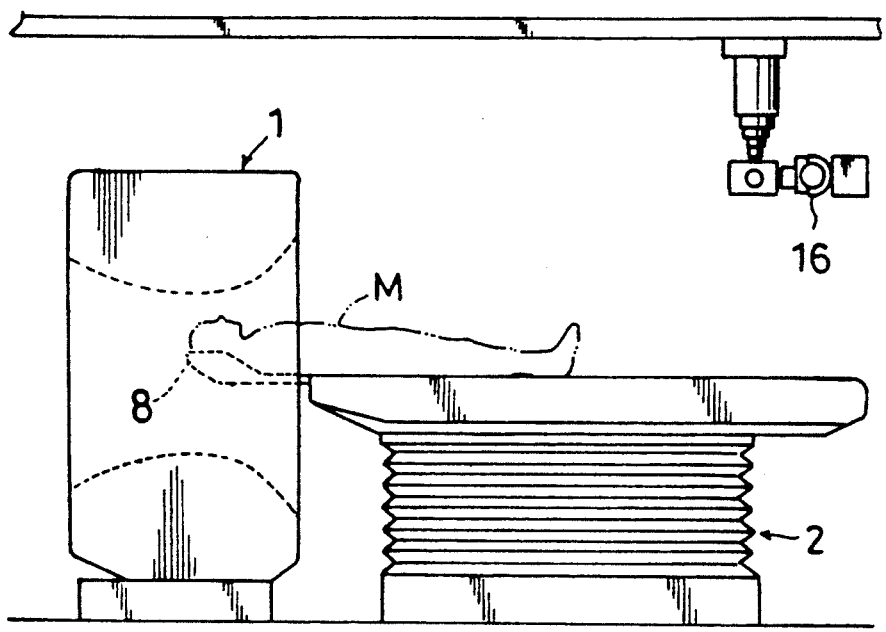
FIG. 6 is a side view showing execution of tomography.

(1) For tomography, the X-ray tube 16 is retracted toward the ceiling as shown in FIG. 6, or retracted to a corner in the examination room. The top board 8 carrying an examinee M is moved horizontally into the gantry 1. A control signal is transmitted from the console 35 to the switching circuit 33 to switch the destination of output of the high voltage unit 34 to the X-ray tube 3 in the gantry 1.

Subsequently, as in operation of a conventional X-ray CT apparatus, X-ray exposure is carried out while revolving the X-ray tube 3 and X-ray detector 4, to collect projection data for forming a slice image.

Figure 7:
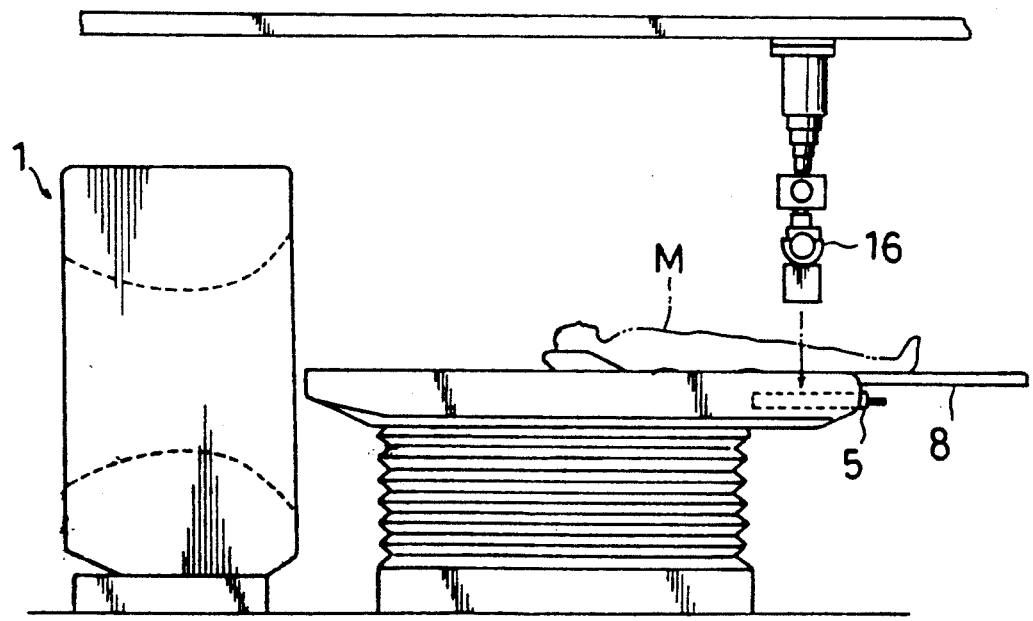
FIG. 7 is a side view showing a mode of ordinary X-ray radiography.

(2-1) For ordinary X-ray radiography with the cassette 5 mounted in the rear position of the bed 2, as shown in FIG. 7, the top board 8 carrying an examinee M is moved horizontally to set the part of the body to be photographed to the position of the cassette 5. The X-ray tube 16 is moved three-dimensionally to a position over the part of the body to be photographed. A control signal is transmitted from the console 35 to the switching circuit 33 to switch the destination of output of the high voltage unit 34 to the X-ray tube 16. X-rays are emitted from the X-ray tube 16 to record a penetration image on the X-ray film contained in the cassette 5.

Figure 8:
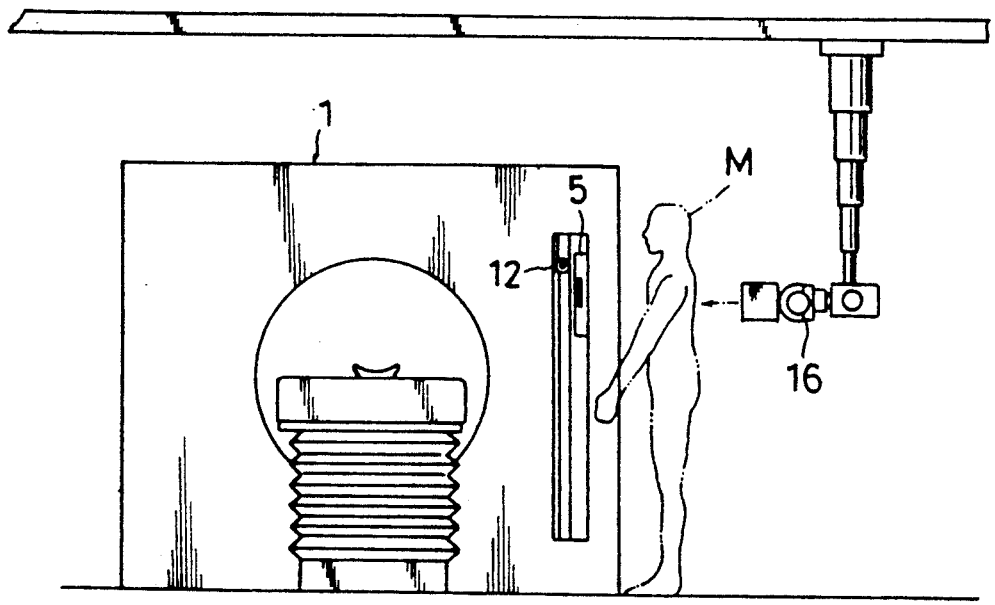
FIG. 8 is a side view showing another mode of ordinary X-ray radiography.

(2-2) For ordinary X-ray photography with the cassette 5 mounted in the front wall of the gantry 1, as shown in FIG. 8, an examinee M is asked to stand by the side wall of the gantry 1. The cassette 5 is slid vertically to a position opposed to the part of the body to be photographed. Then, the cassette 5 is fixed to that position by operating the positioning screw 12. The X-ray tube 16 is moved to a position opposed to the cassette 5. Further, the X-ray tube 16 is turned 90 degrees from the downwardly directed position to set the X-ray emitting direction to the cassette 5. The console 35 is operated to cause the switching circuit 33 to connect the high voltage unit 34 to the X-ray tube 16. X-rays are emitted from the X-ray tube 16 to take a photograph.

Figure 9:
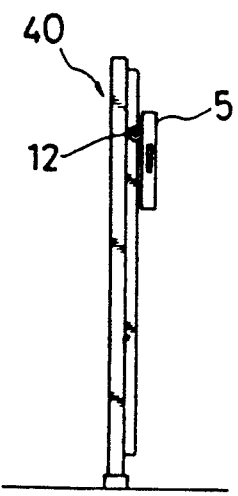
FIG. 9 is a side view showing a different example of cassette mounting.

The mounting position of the cassette 5 is not limited to the above. As shown in FIG. 9, for example, a Bucky's stand r0 may be installed in an appropriate position in the examination room for supporting the cassette 5 to be slidable longitudinally of the stand 40. The slide mechanism shown in FIG. 2 may be applied here also. Further, the cassette 5 may be set between the top board 8 and a part to be photographed of the examinee M lying on the top board 8.

Figure 10:
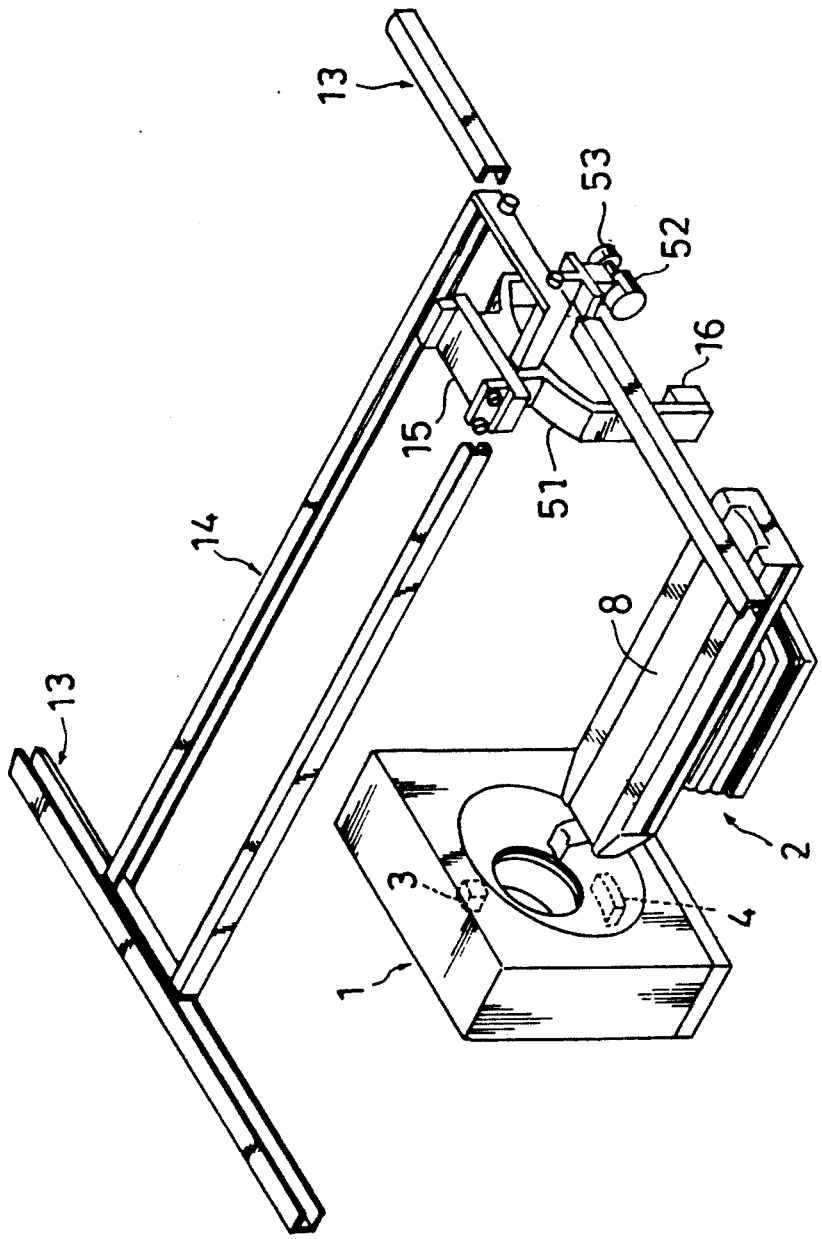
FIG. 10 is a perspective view showing an outward appearance of an X-ray radiographic apparatus in a further embodiment of this invention.

The cassette 5 containing X-ray film may be replaced, for example, with an image intensifier for converting an X-ray image to an optical image. Generally, the image intensifier is large and heavy, and may be difficult to mount in the gantry 1 or the bed 2 as in the embodiment. Then, as shown in FIG. 10, the support block 15 may support a C-shaped arm 51 pivotably connected thereto, with the X-ray tube 16 attached to one end thereof and an image intensifier 52 attached to the other end.

Figure 11:
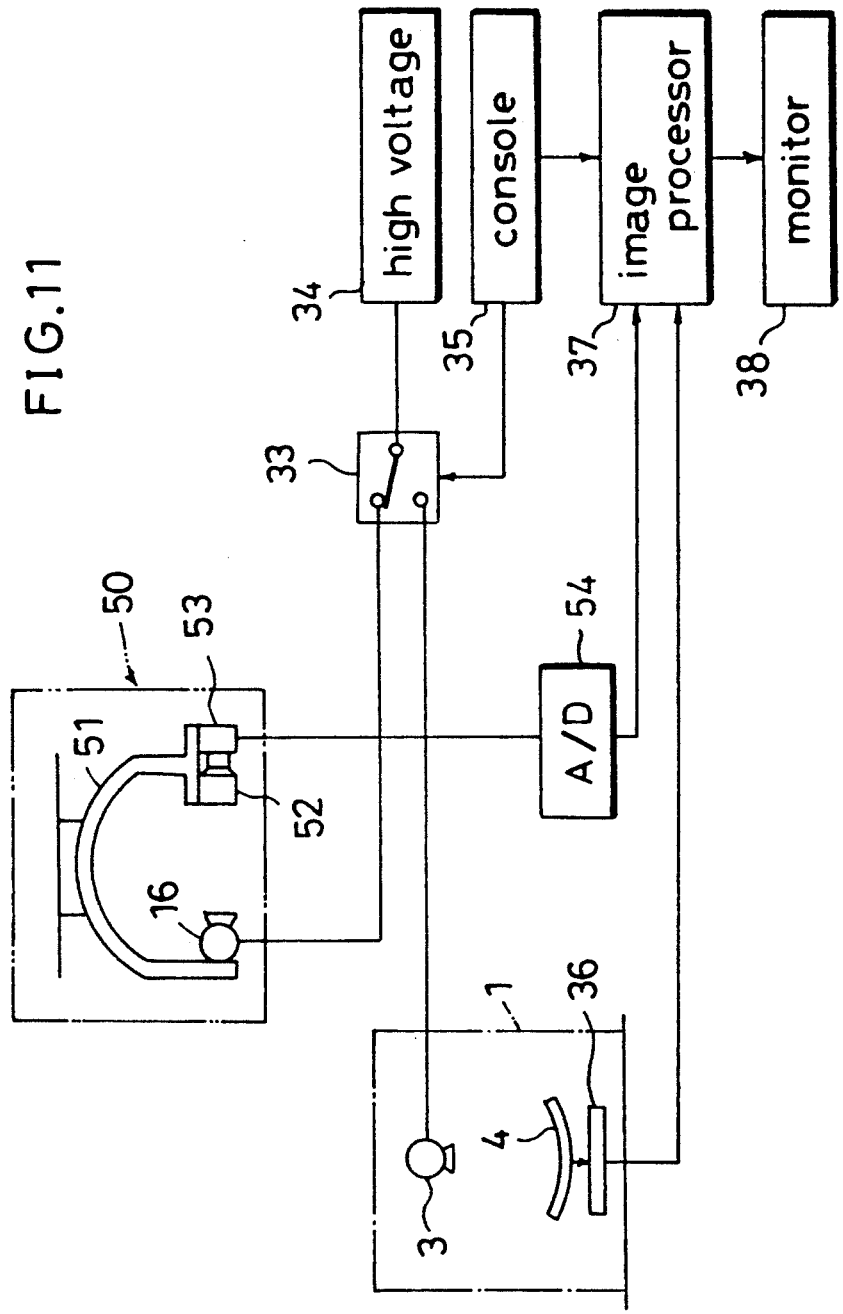
FIG. 11 is a block diagram schematically showing a system configuration of the X-ray radiographic apparatus in the further embodiment.

In this case, as shown in FIG. 11, an X-ray television camera 53 for picking up the optical image outputted from the image intensifier 52 and converting the image to a video signal, and an analog-to-digital converter 54 for converting the video signal to a digital signal, are provided to share the processing function of the image processor 37 to enlarge or reduce images, as well as the X-ray CT apparatus and ordinary X-ray radiographic apparatus (X-ray radiographic apparatus 50 in this case). The console 35 is also shared. It is not essential to support the C-shaped arm 51 in suspension from the ceiling. The C-shaped arm may be moved freely by a moving mechanism installed on the floor, or may be mounted on a support table having caster to be manually movable.

The image intensifier 52 acting as the second X-ray detector may be replaced with a digital sensor having semiconductor detecting elements arranged multidimensionally to detect X-rays The digital sensor is not so large or heavy as the image intensifier, and may be mounted like the cassette 5.

The X-ray tube 16 may be moved manually by the operator instead of relying on the illustrated motor drive.

The present invention may be embodied in other specific forms without departing from the spirit or essential attributes thereof and, accordingly, reference should be made to the appended claims, rather than to the foregoing specification, as indicating the scope of the invention.

What is claimed is:

1. An X-ray radiographic apparatus for medical use in photographing tomographic images and X-ray penetration images of an examinee, said apparatus comprising:
    a bed horizontally movably supporting a top board for carrying the examinee;
    a gantry for X-ray tomography including a first X-ray source revolvable around the examinee, and first X-ray detecting means for detecting transmitted X-rays;
    a second X-ray source mounted on a moving mechanism movable on a three-dimensional coordinate system in an examination room accommodating said bed and said gantry;
    a high voltage unit for supplying an X-ray generating high current to said first X-ray source and said second X-ray source;
    switch means for selecting a destination of output of said high voltage unit; and
    at least one second X-ray detecting means for detecting transmitted X-rays from said second X-ray source.

2. An X-ray radiographic apparatus as defined in claim 1, wherein said second X-ray detecting means comprises a cassette containing X-ray film.

3. An X-ray radiographic apparatus as defined in claim 2, wherein said cassette is mountable in a case movable along a pair of guide rails extending vertically on a wall of said gantry, and fixable to a selected position on said wall.

4. An X-ray radiographic apparatus as defined in claim 3, wherein said case has an X-ray shielding sheet applied to a side surface thereof facing inwardly of said gantry.

5. An X-ray radiographic apparatus as defined in claim 2, wherein said cassette is mountable in said bed.

6. An X-ray radiographic apparatus as defined in claim 2, wherein said cassette is mountable on a Bucky's stand installed in a selected position in said examination room.

7. An X-ray radiographic apparatus as defined in claim 2, wherein said moving mechanism of said second X-ray source includes:
   a ceiling frame secured to a ceiling of said examination room;
   a movable frame movable within said ceiling frame;
   a support block movable within said movable frame in a direction perpendicular to a direction of movement of said movable frame; and
   a vertically extendible and contractible ceiling suspender having an upper end thereof secured to said support block, said second X-ray source being pivotably attached to a lower end of said ceiling suspender.

8. An X-ray radiographic apparatus as defined in claim 1, wherein said second X-ray detecting means comprises an image intensifier for converting transmitted X-rays to an optical image.

9. An X-ray radiographic apparatus as defined in claim 8, wherein said moving mechanism of said second X-ray source includes:
   a ceiling frame secured to a ceiling of said examination room;
   a movable frame movable within said ceiling frame;
   a support block movable within said movable frame in a direction perpendicular to a direction of movement of said movable frame; and
   a C-shaped arm pivotably attached to said support block;
   said second X-ray source being attached to one and of said C-shaped arm, and said image intensifier being attached to the other end of said C-shaped arm.

10. An X-ray radiographic apparatus as defined in claim 1, wherein said second X-ray detecting means comprises a digital sensor having semiconductor elements arranged multidimensionally to detect X-rays.

* * * * *